(12) United States Patent
Ye

(10) Patent No.: US 11,278,646 B2
(45) Date of Patent: Mar. 22, 2022

(54) POROUS MATERIAL

(71) Applicant: CHONGQING RUZER PHARMACEUTICAL CO., LTD, Chongqing (CN)

(72) Inventor: Lei Ye, Chongqing (CN)

(73) Assignee: Chongqing Ruzer Pharmaceutical Co., Ltd, Chongqing (CN)

( * ) Notice: Subject to any disclaimer, the term of this patent is extended or adjusted under 35 U.S.C. 154(b) by 737 days.

(21) Appl. No.: 16/075,994

(22) PCT Filed: Oct. 18, 2016

(86) PCT No.: PCT/CN2016/102455
§ 371 (c)(1),
(2) Date: Aug. 7, 2018

(87) PCT Pub. No.: WO2017/076164
PCT Pub. Date: May 11, 2017

(65) Prior Publication Data
US 2020/0237967 A1    Jul. 30, 2020

(30) Foreign Application Priority Data

Nov. 3, 2015 (CN) .......................... 201510734708.4

(51) Int. Cl.
| A61L 27/56 | (2006.01) |
| A61L 27/04 | (2006.01) |
| A61L 27/06 | (2006.01) |
| A61L 27/12 | (2006.01) |

(52) U.S. Cl.
CPC ............. *A61L 27/56* (2013.01); *A61L 27/047* (2013.01); *A61L 27/06* (2013.01); *A61L 27/12* (2013.01)

(58) Field of Classification Search
CPC ........ A61L 27/56; A61L 27/047; A61L 27/06; A61L 27/12
See application file for complete search history.

(56) References Cited

U.S. PATENT DOCUMENTS

| 6,255,359 | B1 | 7/2001 | Agrawal et al. |
| 2005/0246021 | A1 | 11/2005 | Ringeisen et al. |
| 2010/0010513 | A1 | 1/2010 | Yun et al. |
| 2013/0011691 | A1* | 1/2013 | Ruan ................. B22F 3/1146 428/566 |
| 2013/0251762 | A1 | 9/2013 | Wei et al. |
| 2014/0329323 | A1 | 11/2014 | Nygaard et al. |

FOREIGN PATENT DOCUMENTS

| CN | 101431966 A | 5/2009 |
| CN | 103113129 A | 5/2013 |
| CN | 103230621 A | 8/2013 |
| CN | 103462729 A | 12/2013 |
| CN | 103990182 A | 8/2014 |
| WO | WO 1999032166 A3 | 7/1999 |
| WO | 2010088766 A | 8/2010 |

OTHER PUBLICATIONS

Ochoa Scaffolds for bone tissue engineering, J. of Biomech. p.257, February (Year: 2009).*
The Characterization of Porous Titanium-Niobium Alloy and the Experimental Study of its Biocompatibility.
Office Action issued in CN application No. 201510734708.4, dated Nov. 30, 2017.
Extended European Search Report issued in application No. 16861432.9, dated Aug. 21, 2019.
Chuisheng Zeng, Preparation and Characterization of Porous Bioceramics with Controllable Macrostructure, Medicine & Public Health, Chinese, Selected Doctoral Dissertations and Master's Theses Full-Text Databases (Master), No. 3, Sep. 15, 2004 (Sep. 15, 2004), ISSN: 1671 6779, pp. 50 and 68.
Li, S., Wijn, J., Li, J., Layrolle, P., Groot, K., Macroporous Biphasic Calcium Phosphate Scaffold with High Permeability/Porosity Ratio. Tissue Engineering, 2003, 535-548, 9 (3).
Nauman, E., Fong, K., Keaveny, T., 1999. Dependence of intertrabecular permeability on flow direction and anatomic site. Annals of Biomedical Engineering 27, 517-524.
R.Singh, P.D. Lee, Trevor C. Lindley, R.J. Dashwood, Emilie Ferrie, T. Imwinkelried, Characterization of the structure and permeability of titanium foams for spinal fusion devices. Acta Biomaterialia 5 (2009) 477-487.
D.A.Shimko,V.F. Shimko, E.A. Sander, K.F. Dickson,E. A. Nauman, Effect of Porosity on the Fluid Flow Characteristics and Mechanical Properties of Tantalum Scaffolds,J.Biomed.Mater.Res. B Appl.Biomater.73(2005) 315-324.
Grimm, M., Williams, J., 1997. Measurements of permeability in human calcaneal trabecular bone. Journal of Biomechanics 30 (7), 743-745.

* cited by examiner

*Primary Examiner* — Matthew P Coughlin
*Assistant Examiner* — Thurman Wheeler
(74) *Attorney, Agent, or Firm* — Knobbe Martens Olson & Bear, LLP

(57) ABSTRACT

A porous material of a medical implant material, the material body of which is a hierarchical porous material with multilevel pore cavities graded according a pore size of the material. The permeability of the hierarchical porous material is more than $0.5 \times 10^{-9}$ m$^2$. The hierarchical porous material can fully ensure blood flow, achieve transmission of adequate nutrients and growth factors, migration of cells, and remove cell fragments and stimulate tissue growth, and has various functions, thus fully satisfying the requirements of human tissue regeneration.

6 Claims, No Drawings

POROUS MATERIAL

CROSS REFERENCE TO RELATED APPLICATIONS

This application is the national phase entry of International Application PCT/CN2016/102455, filed on Oct. 18, 2016, which is based upon and claims priority to Chinese Patent Application No. 201510734708.4, filed on Nov. 3, 2015, the entire contents of which are incorporated herein by reference.

TECHNICAL FIELD

The present invention relates to a porous material, in particular to a hierarchical porous material for medical implantation.

BACKGROUND

Loss of human tissues is often caused by injuries or lesions and canceration, which can only be cured by medical implant materials. As a medical implant material, porous material has obvious advantages. The fixation of an implant is more reliable by using a porous structure, which is beneficial for the transmission of nutrient components in human body fluids, reducing an elastic modulus to reduce a stress shielding and can greatly shorten the recovery period of patients. For example, porous titanium is used to prepare hip joints and dental root implants, porous tantalum is used to prepare composite acetabular cups, repair rods for femoral bone necrosis, porous carbonyl apatite and porous bioglass is used for repairing bone defects, which have achieved good effects.

The implant needs a series of features to meet the requirements, including providing mechanical support and promoting tissue regeneration, etc. In these features, permeability is a very important indicator, because after the implant is implanted, a sufficient blood flow is needed for ensuring transmission of adequate nutrients and growth factors and the migration of cells, removing cell fragments, and increasing the potential of tissue conduction, thus stimulating tissue growth. Permeability is one of the main factors affecting the blood flow, the entry of cells into a porous implant, and the diffusion and transmission of nutrients and growth factors. Moreover, in a repair for hard tissue, if the permeability is insufficient, the implant will induce the generation of cartilage tissue instead of hard bone tissue.

In order to meet the requirements of tissue regeneration, the permeability of implant should be high. Currently, reported permeability data of medical implant porous materials, such as the permeability of Z-BCP (porosity is 75%, average pore size is 565 μm) is $0.018 \times 10^{-9}$ m$^2$, the permeability of HA-60 (porosity is 60%, average pore size is 450 pim) is $0.35 \times 10^{-9}$ m$^2$ (Li, S., Wijn, J., Li, J., Layrolle, P., Groot, K., 2003. Macroporous Biphasic Calcium Phosphate Scaffold with High Penneability/Porosity Ratio. Tissue Engineering 9 (3), 535-548.), the permeability of porous titanium (porosity is 78%, average pore size is 488 μm) prepared by pore-forming agent method is $0.389 \times 10^{-9}$ m$^2$ (R. Singh, P. D. Lee, Trevor C. Lindley, R. J. Dashwood, Emilie Ferrie, T. Imwinkelried Characterization of the structure and permeability of titanium foams for spinal fusion devices. Acta Biomaterialia 5 (2009) 477-487), the permeability of porous tantalum (porosity is 80.8%, average pore size is 554 μm) prepared by chemical vapor deposition method is $0.35 \times 10^{-9}$ m$^2$ (D. A. Shimko, V. F. Shimko, E. A. Sander, K. F. Dickson, E. A. Nauman, Effect of Porosity on the Fluid Flow Characteristics and Mechanical Properties of Tantalum Scaffolds, J. Biomed. Mater. Res. B Appl. Biomater. 73 (2005) 315-324), relative to the permeability data values of cancellous bones of human bodies, such as the permeability of the calcaneus cancellous bone is $0.4$-$11.0 \times 10^{-9}$ m$^2$ (Grimm, M., Williams, J., 1997. Measurements of permeability in human calcaneal trabecular bone. Journal of Biomechanics 30 (7), 743-745.), and the permeability of the cancellous bone of the human vertebral body is $1.5$-$2.1 \times 10^{-9}$ m$^2$ (Nauman, E., Fong, K., Keaveny, T., 1999. Dependence of intertrabecular permeability on flow direction and anatomic site. Annals of Biomedical Engineering 27, 517-524.), is low. Therefore, the permeability value of the existing porous materials used as medical implants is low, which is unfavorable for the bone regeneration. Although the problem can be partially solved by increasing the porosity and pore size of the porous materials, the tissue regeneration also has requirements on the pore size of the implanted materials, a larger pore size is not always better. The strength and rigidity of the materials cannot meet the requirements of medical implants if the porosity is too large. Although CN 201210185031 "method for preparing bionic artificial bone with hierarchical (micron/nano) pore structure" provides a hierarchical pore structure implant material, requirements on the permeability are not mentioned, and the permeability of the implant material with the hierarchical pore structure prepared by the method still does not meet the performance requirement of the implant material, in fact, the provided implant material cannot be applied well.

SUMMARY

The objective of the present invention is to provide a new porous material used as a medical implant material. The hierarchical porous material has reasonable structure and good interconnectivity, and the performance index of the permeability can meet the requirements of medical implant materials well.

The objective of the present invention is realized by the following technical solution:

A porous material includes a material body. The material body is a hierarchical porous material with multilevel pore cavities graded according to a pore size of the material. The permeability of the hierarchical porous material is more than $0.5 \times 10^{-9}$ m$^2$.

The above-mentioned hierarchical pore material is used as a medical implant material.

The above-mentioned material body of the hierarchical porous material is constituted by pore cavities at each level graded according to the pore size of the material and cavity walls at each level surrounding to form the pore cavities.

In the pore cavities at any level of the above-mentioned material body, the proportion of the pore cavities interconnecting at least four adjacent pore cavities is more than 85%. Because the hierarchical porous material with this structure has a reasonable interconnectivity design and a good interconnectivity, the permeability of the material is more than $0.5 \times 10^{-9}$ m$^2$.

In the above-mentioned hierarchical porous material, the cavity wall of an upper-level cavity formed by surrounding a three-dimensional space is constituted by a lower-level porous material, the design of the interconnectivity structure is more reasonable and the interconnectivity is better, which is beneficial to increase the permeability of the hierarchical porous material. The permeability of the material can be more than $0.54 \times 10^{-9}$ m$^2$.

Further, the above-mentioned hierarchical porous material used as the medical implant material has a largest level of pore cavities with an average pore size of 200 μm-600 μm, a permeability of more than $0.5 \times 10^{-9}$ m$^2$, and a total porosity of not less than 75%. The hierarchical porous material with this structure is more favorable for cells growth and blood vessels and tissues ingrowth.

Further, the above-mentioned hierarchical porous material used as the medical implant material has a largest level of pore cavities with an average pore size of 300 μm-600 μm. The permeability of the hierarchical porous material is more than $0.57 \times 10^{-9}$ m$^2$.

Further, the above-mentioned hierarchical porous material used as the medical implant material has a largest level of pore cavities with an average pore size of 400 μm-600 μm. The permeability of the hierarchical porous material is more than $0.6 \times 10^{-9}$ m$^2$.

It can be seen that with the increase in the average pore size of the largest level of pore cavities of the hierarchical porous material, the permeability thereof will further increase, which is more beneficial to the invasive growth of cells, blood vessels and tissues.

In any level of pore cavities of the above-mentioned material body, the proportion of pore cavities interconnecting at least four adjacent pore cavities is more than 85%, the cavity wall of an upper-level pore cavity formed by surrounding a three-dimensional space are constituted by a lower-level porous material, and porous material at same level in the material body is a continuous structure, and a maximum outer boundary of the continuous structure formed by the same level of porous materials is equivalent to a maximum space boundary of the entire material body, the permeability of the hierarchical porous material is more than $0.7 \times 10^{-9}$ m$^2$. Because this structure is beneficial to ensure a smooth flow of liquid in the whole interior of the material body.

When pore cavities of the same level of porous material in the above-mentioned porous material are uniform in size and are uniformly distributed in the material body, the permeability of the hierarchical porous material is more than $0.76 \times 10^{-9}$ m$^2$.

When the number of the levels of the hierarchical porous material is three, an average pore size of the pore cavities at a largest level is 200 μm-600 μm, a pore size of a smallest level of pore cavities is a nanoscale, and a pore size of second-level of pore cavities is between the pore size of the largest level of pore cavities and the pore size of the smallest level of pore cavities, when the total porosity of the material is not less than 75%, the permeability of the hierarchical porous material is more than $1.5 \times 10^{-9}$ m$^2$. The permeability of the hierarchical porous material can better meet the application performance requirements of medical implant materials.

The advantages of the present invention are as follows.

(1) The present invention provides a new medical implant hierarchical porous material, which has a reasonable interconnecting structure and a good interconnectivity, enables the permeability to be larger than $0.5 \times 10^{-9}$ m$^2$, and is favorable for meeting the requirements of human implant materials on the permeability, especially when the average pore size of the largest level of pore cavities is 200 μm-600 μm that is suitable for cell growth, the permeability of the hierarchical porous material is still good, thus ensuring sufficient blood flow, transmission of adequate nutrients and growth factors and migration of cells, removing cell fragments, and increasing the potential of tissue conduction, thus stimulating tissue growth and fully satisfying the requirements of human tissue regeneration. The three-level pore structure medical implant porous material with nanoscale pore cavities has many functions and better effects. Tests show that the permeability of the medical implant porous material is significantly improved, and the third-level nanoscale pores can carry many drugs and growth factors, and are beneficial for the adhesion, differentiation and migration of cells, the second-level pores are convenient for the fixation of cells, and the first-level micron pores are convenient for blood vessels and tissues ingrowth.

(2) In the medical implant hierarchical porous material, cavity wall of upper-level pore cavity formed by surrounding a three-dimensional space is constituted by the lower-level porous material, which is favorable for increasing the permeability of the material. The porous material at each same level is the continuous structure, so that the liquid flow channel is continuous and smooth. A maximum outer boundary of the continuous structure formed by the same level of porous materials is equivalent to a maximum space boundary of the entire material body, so that the permeability is further increased, and the material can meet functional requirements in many aspects.

(3) The medical implant porous material has uniform and stable performance and the permeability of the material is further increased due to the uniform size and uniform distribution of the pore cavities at each level thereof.

DETAILED DESCRIPTION

The embodiments of the present invention will be described below. On the premise of the technical solution of the present invention, the detailed implementation and specific operation process are given by the embodiments. However, the scope of the present invention is not limited to the following embodiments.

Embodiments of the present invention are described in detail below.

Embodiment 1

The porous material of this embodiment is porous β-tricalcium phosphate ceramic with a secondary pore structure. An average pore size of large pore cavities is 200 μm, an average pore size of small pore cavities is 560 nm, and the total porosity is 75%. The porosity formed by the large pore cavities is 66% and the porosity formed by the small pore cavities is 9%. The method for preparing porous β-tricalcium phosphate ceramic includes the following steps: mixing the ρ-tricalcium phosphate ceramic powder with an average particle size of 160 nm, urea with an average particle size of 710 nm, and ethyl cellulose with an average particle size of 280 μm according to a volume ratio of 25:10:72 to obtain a mixture, pressing the mixture into a compact green body, performing a vacuum sintering, and then carrying out conventional subsequent treatment according to a β-tricalcium phosphate ceramic process to obtain a porous β-tricalcium phosphate ceramic with secondary structure.

According to National Standard GB/T 1969-1996 method for testing permeability of porous ceramic, a water flow exhaust device is used, and a cylindrical porous β-tricalcium phosphate ceramic sample with a thickness of 10 mm and a cross-sectional diameter of 10 mm is used to be tested at 20° C. The kinematic viscosity of water is $1.006 \times 10^{-6}$ (m$^2$/s). The sample is placed in a clamp to compress the sample, water is introduced from the bottom of the clamp to exhaust the gas inside the clamp completely, the sample clamp is placed in a container with an overflow port. After the water flows out of the overflow port and reaches stability, the time and flow rate will be recorded. The permeability μ is calculated according to the formula $\mu=4Q\eta\delta/(\pi d^2 t\Delta P)$, where Q is the amount of water that has permeated the sample during the test, η is the viscosity of the test water, d is the diameter of the cylindrical sample, δ is the thickness of the cylindrical sample, t is the test time, and ΔP is the pressure difference between two sides of the sample. The permeability of the above-mentioned porous β-tricalcium phosphate with secondary pores is measured to be $0.51 \times 10^{-9}$ $m^2$. The material is used as a bone implant material.

Embodiment 2

The porous material of this embodiment is porous carbonyl apatite with a secondary pore structure. The pore sizes of large pore cavities and small pore cavities thereof are the same as those in Embodiment 1, and the total porosity is 78%. The porosity formed by the large pore cavities is 68% and the porosity formed by the small pore cavities is 10%. The preparation method is similar to that of Embodiment 1.

A flat sample having the size of 20 mm×20 mm×1 mm is prepared from the above-mentioned porous carbonyl apatite sample with secondary pores. A FEINova Nano SEM 400 field emission scanning electron microscope is used for observation. 40 pore cavities are selected randomly from each of the two levels of poles, the interconnection conditions of the pore cavities on the prepared plane with surrounding pore cavities and the interconnection conditions of the internal of the pore cavities with the lower pore cavities are observed. The number of each pore cavity interconnecting adjacent pore cavities is recorded. A result shows that the number of large pore cavities that interconnect more than four adjacent pore cavities is 36 (accounting for 90% of the pore cavities of this level) and the number of small pore cavities that interconnect more than four adjacent pore cavities is 35 (accounting for 87.5% of the pore cavities of this level).

The permeability of the porous carbonyl apatite is measured to be $0.53 \times 10^{-9}$ $m^2$ using the same method as that in Embodiment 1.

Due to the proper proportion of the pore-forming agent, the interconnectivity of each level of pore cavities is ensured, and the effect that the proportion of the pore cavities interconnecting more than four adjacent pore cavities is more than 85% in the pore cavities in this level is achieved, so that the material has a higher permeability index.

The material is used as a bone implant material.

Embodiment 3

The porous material of this embodiment is porous f-tricalcium phosphate ceramic, with a secondary pore structure. The average pore size of large pore cavities is 250 μm, the average pore size of small pore cavities is 600 nm, and the total porosity is 82%. The porosity formed by the large pore cavities is 73% and the porosity formed by the small pore cavities is 9%. The small pore cavities are positioned on the cavity walls of the large pore cavities, and the preparation method is as follows:

(1) Material Preparation

Using β-tricalcium phosphate ceramic powder with an average particle size of 160 nm as a raw material, using urea with an average particle size of 690 nm as a pore-forming agent for the smallest level of pore cavities of the porous β-tricalcium phosphate ceramic to be prepared, and using biological glass powder with an average particle size of 690 nm as a binder, and preparing a slurry according to the volume ratio of β-tricalcium phosphate ceramic powder: urea:biological glass powder:distilled water of 1:3:1:13.

Using polyester foam with a pore size of 600 μm-950 μm, filling the slurry in the polyester foam uniformly by a foam impregnation method to form a green body, drying the green body, and then crushing the green body to obtain mixed grains with a grain size of 50 μm-70 μm containing the raw material, the pore-forming agent and the polyester foam.

(2) Mixing the mixed grains and ethyl cellulose with an average particle size of 330 μm according to a volume ratio of 1:3.5 to obtain a mixture, putting the mixture into a closed mould and pressing the mixture into a compact green body.

(3) Vacuum sintering the compact green body, carrying out a conventional subsequent treatment according to a β-tricalcium phosphate ceramic process on the sintered green body to obtain the porous β-tricalcium phosphate ceramic with a secondary structure.

The crushed polyester foam particles in the mixed grains form channels during sintering, which increases the interconnectivity of the material.

The interconnectivity is tested by the same method as the method in Embodiment 2. Results show that the number of large pore cavities that interconnect more than four adjacent pore cavities is 37 (accounting for 92.5% of the pore cavities of this level) and the number of small pore cavities that interconnect more than four adjacent pore cavities is 36 (accounting for 90% of the pore cavities of this level).

The permeability of the porous β-tricalcium phosphate is measured to be $0.55 \times 10^{-9}$ $m^2$ using the same method as that in Embodiment 1.

The material is used as a bone implant material.

Embodiment 4

The porous material of this embodiment is porous carbonyl apatite with a secondary pore structure. The structure and preparing method are similar to those in Embodiment 3. The average pore size of large pore cavities is 310 μm, the average pore size of small pore cavities is 700 nm, and the total porosity is 86%. The porosity formed by the large pore cavities is 77% and the porosity formed by the small pore cavities is 9%. The interconnectivity is tested by the same method as the method in embodiment 2. Results show that the number of large pore cavities that interconnect more than four adjacent cavities is 37 (accounting for 92.5% of the pore cavities of this level) and the number of small pore cavities that interconnect more than four adjacent cavities is 36 (accounting for 90% of the pore cavities of this level).

The permeability of the porous carbonyl apatite is measured to be $0.58 \times 10^{-9}$ $m^2$ using the same method as that in Embodiment 1. The material is used as a bone implant material.

Embodiment 5

The porous material of this embodiment is porous titanium with a secondary pore structure, which is similar in structure and preparation method to that of Embodiment 3, and the porous materials at each level is a continuous structure, and a maximum outer boundary of the porous material at each level is equivalent to the space boundary of the entire material body. The average pore size of large pore cavities is 600 μm, the average pore size of small pore cavities is 750 nm, and the total porosity is 86%. The porosity formed by the large pore cavities is 76% and the porosity formed by the small pore cavities is 10%. The preparation method is as follows:

(1) Material Preparation

Using titanium powder with an average particle size of 110 nm as a raw material, using methylcellulose with an average particle size of 830 nm as a pore-forming agent for the smallest level of pore cavities of porous titanium to be prepared, using starch with an average particle size of 830 nm as a binder, preparing a slurry according to the volume ratio of titanium powder:methylcellulose:starch:distilled water of 1:3.5:1:13.

Using polyester foam with a pore size of 550 μm-850 μm, filling the slurry in the polyester foam uniformly by a foam impregnation method to form a green body, drying the green body, and then crushing the green body to obtain mixed grains with a grain size of 40 μm-60 μm containing the raw material, the pore-forming agent and the polyester foam.

(2) Mixing the mixed grains and ethyl cellulose with an average particle size of 680 μm according to a volume ratio of 1:4 uniformly to obtain a mixture, putting the mixture into a closed mould and pressing the mixture into a compact green body.

(3) Vacuum sintering the compact green body; carrying out a conventional subsequent treatment according to a titanium process on the sintered green body to obtain the porous titanium with a secondary structure.

The interconnectivity is tested by the same method as the method in Embodiment 2. Results show that the number of large pore cavities that interconnect more than four adjacent cavities is 37 (accounting for 92.5% of the pore cavities of this level) and the number of small pore cavities that interconnect more than four adjacent cavities is 36 (accounting for 90% of the pore cavities of this level).

The permeability of the above-mentioned porous titanium with secondary pores is measured to be $0.71 \times 10^{-9}$ m$^2$ using the same method as that in Embodiment 1. The material is used as a bone implant material.

Embodiment 6

The medical implant porous material of this embodiment is porous titanium with a secondary pore structure, which is similar to that of Embodiment 4, the difference is that during preparation, the particle size error of the methylcellulose and the ethyl cellulose is controlled within 10%, so that the prepared porous titanium has a uniform pore size and small error. The mixed grains and ethyl cellulose are repeatedly stirred, fully and uniformly mixed, so that the pore cavities are uniformly distributed. The interconnectivity is tested by the same method as the method in Embodiment 2. Results show that the number of large pore cavities that interconnect more than four adjacent cavities is 37 (accounting for 92.5% of the pore cavities of this level) and the number of small pore cavities that interconnect more than four adjacent cavities is 37 (accounting for 92.5% of the pore cavities of this level).

The permeability of the porous titanium with secondary pores is measured to be $0.77 \times 10^{-9}$ m$^2$ using the same method as that in Embodiment 1. The material is used as a bone implant material.

Embodiment 7

The medical implant porous material of this embodiment is porous tantalum with a tertiary pore structure, the cavity walls of the first-level pore cavities (i.e., the largest-level pore cavities) are provided with second-level pore cavities which are distributed evenly and interconnected, and the cavity walls of the second-level pore cavities are provided with third-level pore cavities (i.e., the smallest-level pore cavities) which are distributed evenly and interconnected. The pore cavities at each level are interconnected. The porous tantalum at each level is a continuous structure, and a maximum outer boundary of the porous tantalum at each level is equivalent to the space boundary of the entire material body. An average pore size of third-level pore cavities is 64 nm, an average pore size of second-level pore cavities is 96 μm, an average of first-level pore cavities is 600 μm, and the total porosity is 93%. The porosity formed by the first-level pore cavities is 80%, the porosity formed by the second-level pore cavities is 8%, and the porosity formed by the third-level pore cavities is 5%.

The preparation method is:

(1) Material Preparation

Using tantalum powder with an average particle size of 20 nm as a raw material, using starch with an average particle size of 75 nm as a pore-forming agent for the smallest level of pore cavities of porous tantalum to be prepared, using stearate with an average particle size of 75 nm as a binder, preparing a slurry according to the volume ratio of tantalum powder:starch:stearate:distilled water of 1:4:1:11.

Using polyester foam with a pore size of 550 μm-820 μm, filling the slurry in the polyester foam uniformly by a foam impregnation method to form a green body, drying the green body, and then crushing the green body to obtain mixed grains with a grain size of 60 μm-80 μm containing the raw material, the pore-forming agent and the polyester foam.

(2) fully and uniformly mixing the mixed grains and ammonium chloride with an average particle size of 110 μm according to a volume ratio of 1:4 to obtain a mixture, pouring the mixture into a three-dimensional interconnecting polyester foam with an average strut diameter of 710 μm and an average pore size of 670 μm, and then putting the polyester foam into a closed mould to press the polyester foam into a compact green body.

(3) Vacuum sintering the compact green body, carrying out a conventional subsequent treatment according to tantalum material process on the sintered green body to obtain the porous tantalum with a tertiary structure.

The interconnectivity is tested by the same method as the method in Embodiment 2. Results show that the number of pore cavities that interconnect more than four adjacent cavities is as follows. The number of the first-level pore cavities is 38 (accounting for 95% of the pore cavities of this level), the number of the second-level pore cavities is 37 (accounting for 92.5% of the pore cavities of this level), and the number of the third-level pore cavities is 37 (accounting for 92.5% of the pore cavities of this level).

The permeability of the above-mentioned porous tantalum with tertiary pores is measured to be $1.52 \times 10^{-9}$ m$^2$ using the same method as that in Embodiment 1. The material is used as a bone implant material.

Embodiment 8

The medical implant porous material of this embodiment is porous tantalum with a tertiary pore structure, which is similar to that of Embodiment 8, but during preparation, in step (2), a three-dimensional interconnecting polyester foam with an average pore size of 600 μm is used, and the total porosity of the prepared porous tantalum is 95%, the porosity formed by the first-level pore cavities is 82%, the porosity formed by the second-level pore cavities is 8%, and the porosity formed by the third-level pore cavities is 5%.

The interconnectivity is tested by the same method as the method in Embodiment 2. Results show that the number of pore cavities that interconnect more than four adjacent cavities is as follows. The number of the first-level pore cavities is 38 (accounting for 95% of the pore cavities of this level), the number of the second-level pore cavities is 38 (accounting for 95% of the pore cavities of this level), and the number of the third-level pore cavities is 37 (accounting for 92.5% of the pore cavities of this level). The permeability of the porous tantalum is measured to $1.57 \times 10^{-9}$ m$^2$ using the same method as that in Embodiment 1. The material is used as a bone implant material.

What is claimed is:

1. A porous material, comprising:
   a material body, wherein
   the material body is a hierarchical porous material with pore cavities at multilevel graded according to a pore size of the porous material; and
   wherein the material body of the hierarchical porous material is constituted by the pore cavities at each level graded according to the pore size of the porous material and cavity walls at each level surrounding to form the pore cavities;
   wherein a cavity wall of an upper-level pore cavity formed by surrounding a three-dimensional space is constituted by a porous material of a lower-level pore cavity such that the lower-level pore cavity are positioned within the cavity wall of the upper-level pore cavity,
   wherein porous materials at each same level of the material body is a continuous structure, and a maximum outer boundary of the continuous structure formed by the same level of porous material is equivalent to a maximum space boundary of the entire material body; and the permeability of the porous material is more than $0.7 \times 10^{-9}$ m$^2$; and
   wherein the porous material is porous tantalum.

2. The porous material according to claim 1, wherein pore cavities of the porous material at each same level in the hierarchical porous material are uniform in size and are uniformly distributed in the material body; and the permeability of the hierarchical porous material is more than $0.76 \times 10^{-9}$ m$^2$.

3. The porous material according to claim 1, wherein when a number of the levels of the hierarchical porous material is three, a pore size of smallest-level pore cavities is a nanoscale, and a pore size of second-level pore cavities is between a pore size of largest-level pore cavities and the pore size of the smallest-level pore cavities; the permeability of the hierarchical porous material is more than $1.5 \times 10^{-9}$ m$^2$.

4. The porous material according to claim 1, wherein the porous material is used as a medical implant material, wherein porous materials at each same level of the material body is a continuous structure, and a maximum outer boundary of the continuous structure formed by the same level of porous material is equivalent to a maximum space boundary of the entire material body; and the permeability of the hierarchical porous material is more than $0.7 \times 10^{-9}$ m$^2$.

5. The porous material according to claim 4, wherein pore cavities of the porous material at each same level in the hierarchical porous material are uniform in size and are uniformly distributed in the material body; and the permeability of the hierarchical porous material is more than $0.76 \times 10^{-9}$ m$^2$.

6. The porous material according to claim 5, wherein when a number of the levels of the hierarchical porous material is three, a pore size of smallest-level pore cavities is a nanoscale, and a pore size of second-level pore cavities is between a pore size of largest-level pore cavities and the pore size of the smallest-level pore cavities; the permeability of the hierarchical porous material is more than $1.5 \times 10^{-9}$ m$^2$.

* * * * *